(12) United States Patent
Lagerborg et al.

(10) Patent No.: US 8,646,448 B2
(45) Date of Patent: Feb. 11, 2014

(54) EMG-CONTROLLED VENTILATOR AND METHOD FOR THE OPERATION THEREOF

(75) Inventors: Johan Lagerborg, Rönninge (SE); Joakim Laksov, Danderyd (SE)

(73) Assignee: Maquet Critical Care AB, Solna (SE)

( * ) Notice: Subject to any disclaimer, the term of this patent is extended or adjusted under 35 U.S.C. 154(b) by 753 days.

(21) Appl. No.: 12/597,520

(22) PCT Filed: Apr. 27, 2007

(86) PCT No.: PCT/EP2007/054156
§ 371 (c)(1),
(2), (4) Date: Apr. 20, 2010

(87) PCT Pub. No.: WO2008/131798
PCT Pub. Date: Nov. 6, 2008

(65) Prior Publication Data
US 2010/0252038 A1    Oct. 7, 2010

(51) Int. Cl.
*F16K 31/02* (2006.01)
*A61M 16/00* (2006.01)
*A62B 7/00* (2006.01)

(52) U.S. Cl.
USPC ............ 128/204.23; 128/200.24; 128/202.22; 128/202.27; 128/203.14; 128/204.21; 128/205.23

(58) Field of Classification Search
None
See application file for complete search history.

(56) References Cited

U.S. PATENT DOCUMENTS

| | | | |
|---|---|---|---|
| 5,820,560 A | 10/1998 | Sinderby et al. | |
| 6,349,724 B1 * | 2/2002 | Burton et al. | 128/204.18 |
| 6,411,843 B1 | 6/2002 | Zarychta | |
| 6,588,423 B1 | 7/2003 | Sinderby | |
| 2003/0000526 A1 | 1/2003 | Gobel | |
| 2003/0100843 A1 | 5/2003 | Hoffman | |
| 2008/0308104 A1 | 12/2008 | Blomberg et al. | |

FOREIGN PATENT DOCUMENTS

| | | |
|---|---|---|
| EP | 0 324 275 | 7/1989 |
| EP | 0 774 269 A1 | 10/1996 |
| WO | WO 2004/078246 | 9/2004 |

* cited by examiner

*Primary Examiner* — Loan Thanh
*Assistant Examiner* — Joshua Lee
(74) *Attorney, Agent, or Firm* — Schiff Hardin LLP

(57) ABSTRACT

A ventilator provides breathing support to a patient in an EMG controlled mode, and has an input that receives an EMG signal representative of breathing activity from the patient and a control unit for controlling the ventilation in dependence of said EMG signal. The ventilator has a registration unit that registers the actual breathing support provided from the ventilator to the patient, and the control unit determines if there is asynchrony between the EMG signal and the breathing activity and, in case of asynchrony, causes a switch from EMG controlled ventilation to a second ventilation mode not dependent on the EMG signal. If synchrony is detected the ventilator can return to EMG controlled ventilation.

30 Claims, 3 Drawing Sheets

EMG-CONTROLLED VENTILATOR AND METHOD FOR THE OPERATION THEREOF

BACKGROUND OF THE INVENTION

1. Field of the Invention

The present invention relates to a ventilator and a method for providing breathing support in EMG controlled mode.

2. Description of the Prior Art

Ventilators are used to support breathing in patients are unable to breathe or whose breathing function is insufficient. Traditionally two different modes have been used. If the patient shows some breathing activity a support mode such as pressure support or volume support mode can be used, in which the patient's attempts to inhale are used to trigger an inspiration phase in the ventilator. If the patient shows no breathing activity controlled mechanical ventilation mode must be used, in which a respiratory rate is determined without any input from the patient.

Recently, ventilators have been disclosed that are neurally controlled, that is, controlled in dependence on an electromyographic signal related to breathing. For example, U.S. Pat. No. 6,588,423 describes a ventilator that is controlled on the basis of an EMG signal from the diaphragm, referred to as an Edi signal (Electrical activity of the diaphragm). The EMG signal may be registered, for example by means of an esophageal catheter in a manner well known in the art.

In some cases the detected EMG signal does not reflect correctly the actual breathing phases of the patient. In such cases there may be a mismatch when the ventilator tries to supply air to the patient while the patient is trying to exhale.

SUMMARY OF THE INVENTION

It is an object of the invention to provide an improved ventilator and a method of controlling a ventilator based on EMG control.

This object is achieved according to the present invention by a ventilator arranged to provide breathing support to a patient in EMG controlled mode, having an input that receives an EMG signal representative of breathing activity from the patient, and a control unit for controlling the ventilation, i.e. controlling operation of the breathing circuit of the ventilator, in dependence on the EMG signal, the ventilator also having a registration unit that registers the actual breathing support provided from the ventilator to the patient. The control unit determines if there is asynchrony between the EMG signal and the breathing activity and, in case of asynchrony, either automatically switches operation of the breathing circuit from EMG controlled ventilation to a second ventilation mode not dependent on the EMG signal, or emits an alarm to prompt a manual switch.

The object is also achieved by a method for providing EMG controlled breathing support to a patient, including the following steps:

receiving an EMG signal representative of breathing activity from the patient and controlling the ventilation in dependence of the EMG signal, registering the actual breathing support provided from the ventilator to the patient, automatically determining if there is asynchrony between the EMG signal and the breathing activity, and in case of asynchrony, switching from EMG controlled ventilation to a second ventilation mode not dependent on the EMG signal.

Hence, according to the invention, the signal received from the esophageal catheter will only be used to control the ventilator if it is found that the signal truly represents the breathing activity of the diaphragm. If the signal is found to be inconsistent with the patient's own breathing activity, the ventilator will be controlled in another ventilation mode. Thus, the apparatus and method according to the invention ensure that if the signal from the esophageal catheter will not be used if it is inconsistent with the patient's own breathing rhythm. This may be the case, for example if the catheter is placed incorrectly within the patient, or because of other disturbances or artefacts. As used herein, the term EMG controlled mode means a support mode in which the ventilation support is based on the EMG signal from the diaphragm.

The control unit is preferably arranged to automatically switch to a support mode as the second mode. The switch may also be performed manually, in which case an alarm is issued if an asynchrony is detected, to prompt an operator to perform the switch.

In a first embodiment the control unit is configured to determine whether an asynchrony is present based on a relationship between the inspiration time and total breath time for at least one breath as determined from the EMG signal or based on a relationship between the inspiration time and expiration time for at least one breath as determined from the EMG signal. These relationships normally lie within a well-defined interval. If they are outside of this interval, in particular, if the inspiration time is too long compared to the expiration time or the total time for one breath, this is an indication that something is wrong.

Alternatively, the control unit is configured to determine whether an asynchrony is present based on a comparison of the actual respiratory rate provided by the ventilator and the respiratory rate calculated on the basis of the EMG signal. These two methods of detecting asynchrony are preferably used together for increased security.

When the ventilator is ventilating in the second ventilation mode, the control unit may be configured to switch to EMG controlled mode if the EMG signal is found to be synchronous with the patient's breathing activity.

DESCRIPTION OF THE PREFERRED EMBODIMENTS

Figure 1:
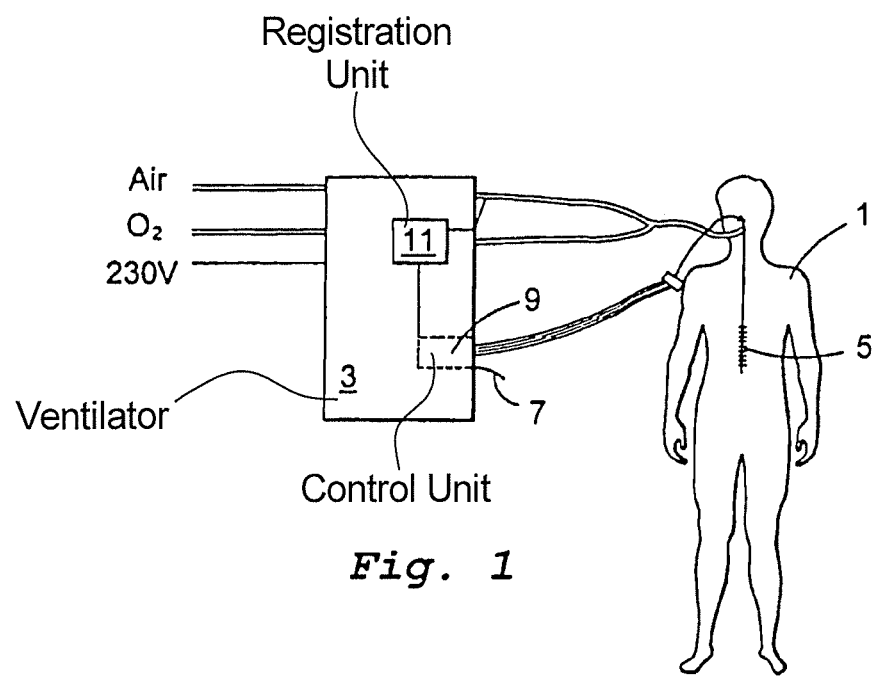
FIG. 1 illustrates a patient with an oesophageal catheter used to control a ventilator.

FIG. 1 is a schematic overview of a patient 1 connected to a ventilator 3 and having an esophageal catheter 5 inserted in order to record a myoelectric signal from the diaphragm. This myoelectric signal (EMG signal) is fed to a control input 7 of the ventilator 3 to control the ventilating function of the patient 1. The catheter 5 carries a number of electrodes, for example, nine electrodes placed equidistantly in an array along the catheter to produce eight subsignals, each subsignal being a difference signal between two neighbouring electrodes. The subsignals will be processed in a control unit 9 in the ventilator to produce the overall signal that can be used to control the ventilator.

The ventilator 3, as is known, includes a breathing circuit that is operable in a number of selectable modes in order to provide breathing assistance (support) to the patient 1.

In some cases the EMG signal will not correctly reflect the diaphragm activity. This may be the case if the catheter is inserted too far, or not far enough, into the patient's oesophagus, so that it will pick up signals from other muscles than the diaphragm, or no signal at all. If inserted to far, the catheter may pick up signals from expiratory muscles instead of the inspiratory activity of the diaphragm. In this case the EMG signal will have the opposite phase of the patient's actual breathing activity. The ventilator will then be triggered to start an inspiration while the patient is expiring and vice versa. There may also be other disturbances or leakages that will cause the EMG signal to deviate from the patient's breathing rate. According to the invention the ventilator has a registration unit 11 for registering the actual breathing support provided to the patient from the ventilator and provide them to the control unit 9. The control unit 9 is arranged to determine asynchrony between the EMG signal and the patient's own breathing activity based on the signal from the registration unit 11 and the Edi signal. If asynchrony is detected, the control unit 9 causes the breathing circuit of the ventilator 3 to switch from an EMG controlled mode to a ventilation mode that is not dependent on the EMG signal. Such a mode will generally be referred to as a support mode herein.

Figure 2A:
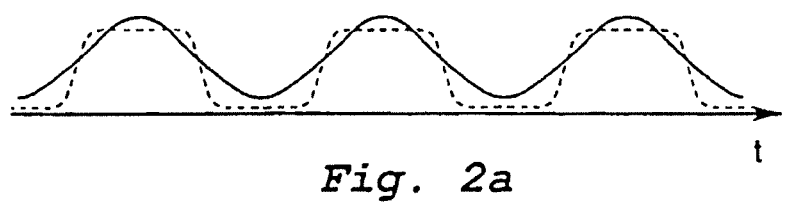
FIG. 2 illustrates the ideal situation of EMG controlled ventilation.

FIG. 2a illustrates an ideal situation in which the EMG signal, shown as a solid line along a time axis t, corresponds to the Edi signal. The ventilator curve is shown as a dashed line. As can be seen, the ventilator will trigger inspiration when the patient is actually trying to breathe in, and cycle off when the patient is actually trying to exhale.

Figure 2B:
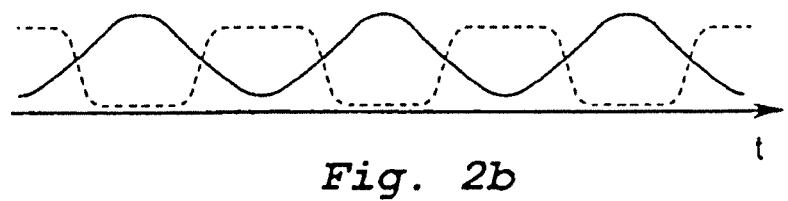

FIG. 2b illustrates a situation in which the EMG signal, shown as a solid line is not in the same phase as the ventilator curve, shown as a dashed line, which represents the support provided to the patient.

Figure 3:
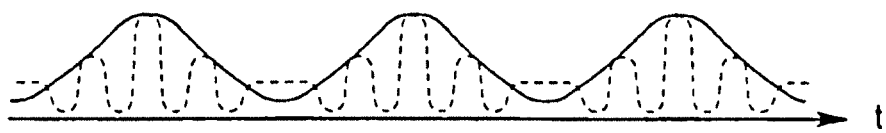
FIG. 3 illustrates EMG controlled ventilation when the EMG signal does not reflect the patient's breathing activity.

FIG. 3 illustrates a situation in which the EMG signal used to control the breathing support has the opposite phase of the patient's own breathing. In this case the breathing support, if in EMG mode, will work against the patient's own breathing cycle. This may be the case, for example, if the oesophageal catheter is inserted too far into the patient's stomach so that the EMG from expiratory muscles in the abdomen is detected instead of the diaphragm. Again, the EMG signal is shown as a solid line while a dashed curve indicates the breathing support supplied by the ventilator.

The triggering method uses both EMG and airway inspiratory flow or pressure. The decisions for triggering and cycling off will be made by a logic circuit on a "first come, first served" basis, as disclosed in U.S. Pat. No. 6,588,423, col. 12. In this case, while the ventilator is trying to supply air to the patient, the patient will generate an expiratory pressure that will work in the opposite direction. The magnitude of the expiratory pressure will vary depending on the patient's condition. When the expiratory pressure becomes too high, the patient will exhale despite the air supplied by the ventilator. As shown in FIG. 3, the resulting curve for the breathing support delivered by the ventilator will vary with a higher frequency than the actual respiratory rate of the patient, that is, the patient will experience several short breaths instead of one proper breath.

Figure 4:
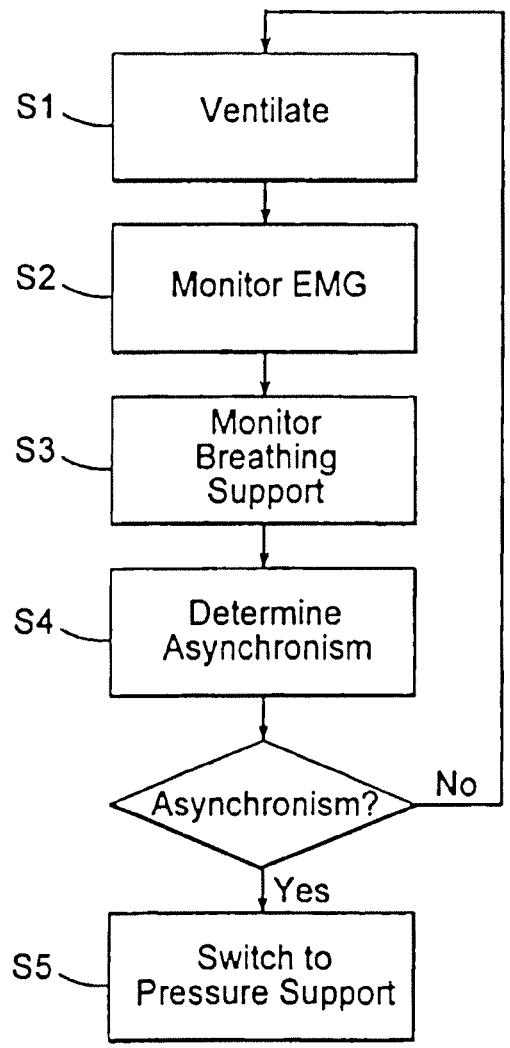
FIG. 4 is a flow chart of the inventive method.

FIG. 4 is a flow chart of the inventive method while EMG controlled ventilation is provided to the patient.

Step S1: Ventilate patient in EMG controlled mode.

Step S2: Monitor the EMG signal used to control the ventilator.

Step S3: Monitor the breathing support supplied by the ventilator to the patient.

Step S4: Determine synchrony or asynchrony of the EMG signal and breathing support.

Step S5: If asynchrony is detected, switch to a support mode for the ventilation; if not, repeat procedure.

Although they are shown in FIG. 4 as consecutive steps, it will be understood that steps S1 is performed until a switch to a support mode is made. Steps S2 and S3 are performed in parallel to enable the comparison performed in step S4. As an alternative, in Step S5 an alarm may be issued if asynchrony is detected, to prompt an operator to switch ventilation modes manually.

Two main principles are proposed for the detection of asynchrony in step S4. The first principle is based on inspiratory and expiratory phases as determined from the Edi signal. According to this first principle the relationship between the duration of the inspiratory phase and the duration of the total time required for an inspiratory and expiratory phase is used to detect asynchrony. As will be understood by the skilled person, the relationship between the duration of the inspiratory phase and the duration of the expiratory phase will serve as an indicator in substantially the same way. The second principle is based on a comparison between the actual respiratory rate delivered by the ventilator and the respiratory rate that would have been delivered by the ventilator if the patient had had no pneumatic activity.

The first principle mentioned above, is based on the assumption that the duration of the inspiratory time $T_i$ will be relatively normal whereas the expiratory time $T_e$ will be shortened. Hence, the relationship between $T_i$ and the total time for one breath $T_{tot}=T_i+T_e$ will be greater than normal in this case. An increase in the relationships $T_i/T_{tot}$ or $T_i/T_e$ may indicate that the EMG signal that is recorded is not representative of the activity of the diaphragm, but instead of some other muscle or muscles, for example, expiratory muscles in the abdomen. It may also indicate that the EMG signal is affected by noise or other artefacts. Hence, in this case, the EMG signal supplied to the ventilator is not suitable for controlling the patient's breathing. In this case, as indicated above, the control mode of the ventilator should be switched from EMG controlled mode to a ventilation mode not dependent on the EMG signal, preferably a support mode.

With this first principle a number of breaths may be considered instead of just one breath. This may be done in several different ways. The values $T_i$, $T_e$ and/or $T_{tot}$ for two or more breaths may be used to calculate sums or average values $T_{iav}$, $T_{eav}$ and/or $T_{totav}$ which can be used to obtain more reliable values than those obtained from only one breath. Alternatively, $T_i{:}T_e$ and/or $T_i{:}T_{tot}$ may be determined for a number of breaths individually but considered together. If a certain fraction (for example, two out of three, or three out of five) of the breaths exhibit a too high $T_i{:}T_e$ or $T_i{:}T_{tot}$, this will be taken to indicate that there is a mismatch between the phases of the patient's own breathing activity and the breathing support provided by the ventilator. Alternatively, after a certain number of consecutive breaths exhibit a too high $T_i{:}T_e$ or $T_i{:}T_{tot}$, a mismatch will be considered to have been detected.

The second principle is based on the fact that if the phases of the patient and the ventilator do not match, the breathing support provided by the ventilator will be influenced both by the EMG signal used to control the ventilator and by the actual pressure generated by the patient. Hence, the respiratory rate that would be delivered by the ventilator if the patient showed no pneumatic activity would be lower than the actual respiratory rate of the ventilator. In other words, as can be seen from FIG. 3, the patient will breathe more frequently than if the ventilator had been controlled by only the EMG signal.

Hence, according to the second principle asynchrony may be detected according to the following:

Determine the respiratory rate of the breathing support actually provided by the ventilator and the respiratory rate determined by the EMG signal. The latter respiratory rate is the one that would be provided by the ventilator if there was no pneumatic influence from the patient.

Compare the two respiratory rates to each other. If the patient and the ventilator are in phase these two respiratory rates will be approximately the same. If there are disturbances the two respiratory rates will differ from each other. A threshold may be set, defining the difference that will be acceptable. If the breathing rates differ by more than the threshold value an asynchrony is detected. The threshold value may be an absolute value, or may be determined as a fraction of the actual respiratory rate. A combination of an absolute value and a fraction may also be applied.

This second principle can only be used in an efficient manner if the patient's own breathing condition is strong enough to trigger and/or cycle off pneumatically. If this is not the case the patient's breathing activity will not influence the ventilator's respiratory rate to a sufficient degree. The first and the second principle for detecting asynchrony may be applied together, to increase security.

Figure 5:
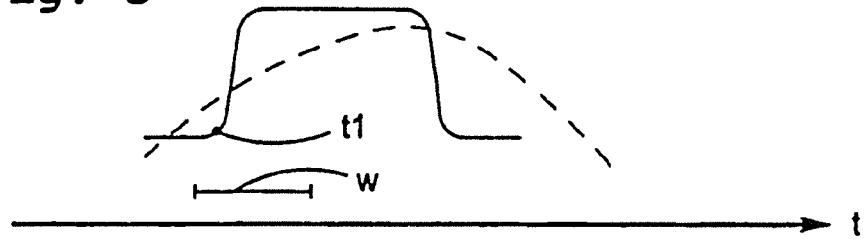
FIG. 5 illustrates the use of the inventive method when a support ventilation mode has been activated.

In the situation when the ventilator mode has been switched to a support mode according to the procedure of FIG. 4, the synchrony between the EMG signal and the patient's own breathing activity is preferably monitored to determine if the ventilator can return to EMG controlled mode. One method of doing this is illustrated in FIG. 5. Again, the Edi signal is shown as a solid line while the ventilator support is shown as a dashed line. The starting point of an inspiration triggered by the ventilator is marked t1. A window W is defined around the starting point of the pneumatic triggering. Synchrony is determined to exist if the Edi signal starts to indicate an inspiration some time within the window. Preferably the length of the window is determined based on the inspiration time Ti, for example as half the inspiration time Ti. This inspiration time is preferably determined based on a number of preceding breaths. The length of the window may also be determined as a fix time, or in relation to expiration time. Further, absolute minimum and maximum duration for the window may be set. An example of such minimum and maximum durations may be 65 ms and 200 ms, respectively.

The method of synchrony detection as described above can be improved by simultaneously monitoring Ti/Ttot as described above in connection with asynchrony detection. In this way it can be ensured that the ventilator does not switch to EMG controlled mode if there is not true synchrony. In particular, if Ti/Ttot is used to detect asynchrony using the same criterion to detect synchrony will help avoid an undue return to EMG controlled mode.

Figure 6:
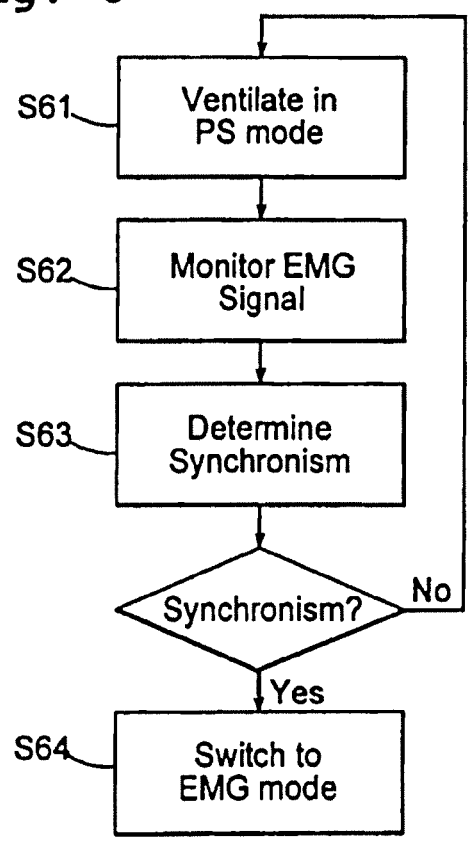
FIG. 6 is a flowchart of the method according to the invention while providing pneumatic support ventilation to the patient by a ventilator that is also capable of operation in an EMG-controlled mode.

FIG. 6 is a flow chart of the inventive method while pneumatic support ventilation is provided to the patient by a ventilator that is also capable of EMG controlled mode.

Step S61: Ventilate patient in a support mode.

Step S62: Monitor the EMG signal received from the patient.

Step S63: Determine synchrony or asynchrony of the EMG signal and breathing support.

Step S64: If synchrony is detected, switch to EMG controlled mode for the ventilation; if not, repeat procedure.

Of course, the procedure of FIG. 6 may be performed also if the ventilation starts in a support mode. It is not a prerequisite that a switch from EMG controlled mode has been made first.

Although modifications and changes may be suggested by those skilled in the art, it is the intention of the inventors to embody within the patent warranted hereon all changes and modifications as reasonably and properly come within the scope of their contribution to the art.

We claim as our invention:

1. A ventilator comprising:
   a breathing circuit adapted to interact with a patient, said breathing circuit being operable in a plurality of different modes to provide breathing assistance to the patient as actual breathing support generated in the breathing circuit and delivered to the patient as an output of the breathing circuit, including an EMG-controlled mode and a non-EMG-controlled mode;
   a control unit that operates said breathing circuit in a selected one of said plurality of modes;
   a registration unit that registers said actual breathing support provided by the breathing circuit to the patient; and
   said control unit being connected to said registration unit and being supplied with an EMG signal from the patient, said control unit being configured to determine, from an output of said registration unit and said EMG signal, whether an asynchrony exists based on a time relationship between said EMG signal and said actual breathing support and, if said asynchrony is determined to exist while said control unit is operating said breathing circuit in said EMG-controlled mode, said control unit being configured to cause a switch from operation of said breathing circuit in said EMG controlled mode to operation in said non-EMG-controlled mode.

2. A ventilator as claimed in claim 1 wherein said control unit is configured to cause switching of said breathing circuit to a support ventilation mode, as said non-EMG-controlled mode.

3. A ventilator as claimed in claim 1 wherein said control unit is configured to determine whether said asynchrony is present based on a relationship between inspiration time and total breath time for at least one breath determined from said EMG signal.

4. A ventilator as claimed in claim 1 wherein said control unit is configured to determine whether said asynchrony is present based on a relationship between inspiration time and expiration time for at least one breath determined from said EMG signal.

5. A ventilator as claimed in claim 1 wherein said control unit is configured to switch operation of said breathing circuit from said non-EMG-controlled mode back to said EMG-controlled mode if said control unit detects synchrony between said EMG signal and said breathing activity while said breathing circuit is being operated in said non-EMG-controlled mode.

6. A ventilator as claimed in claim 1 wherein said control unit is configured to automatically switch operation of said breathing circuit from said EMG-controlled mode to said non-EMG controlled mode, with no manual intervention.

7. A method for providing breathing assistance to a patient, comprising the steps of:
   operating a breathing circuit to interact with a patient in selected one of a plurality of different modes to provide breathing assistance to the patient as actual breathing support generated in the breathing circuit and delivered to the patient as an output of the breathing circuit, including an EMG-controlled mode and a non-EMG-controlled mode;

in a registration unit, automatically registering said actual breathing support provided by the breathing circuit to the patient; and supplying a control unit connected to said registration unit with an EMG signal from the patient and with an output from said registration unit and, in said control unit, automatically determining, from said output of said registration unit signal and said EMG signal, whether an asynchrony exists based on a time relationship between said EMG signal and said actual breathing support and, if said asynchrony is determined to exist while said breathing circuit is operating in said EMG-controlled mode causing, from said control unit, a switch from operation of said breathing circuit in said EMG controlled mode to operation in said non-EMG-controlled mode.

8. A method as claimed in claim 7 comprising, from said control unit, causing switching of said breathing circuit to a support ventilation mode, as said non-EMG-controlled mode.

9. A method as claimed in claim 7 comprising, in said control unit, determining whether said asynchrony is present based on a relationship between inspiration time and total breath time for at least one breath determined from said EMG signal.

10. A method as claimed in claim 7 comprising in said control unit, determining whether said asynchrony is present based on a relationship between inspiration time and expiration time for at least one breath determined from said EMG signal.

11. A method as claimed in claim 7 comprising, from said control unit, causing a switch in operation of said breathing circuit from said non-EMG-controlled mode back to said EMG-controlled mode if said control unit detects synchrony between said EMG signal and said breathing activity while said breathing circuit is being operated in said non-EMG-controlled mode.

12. A method as claimed in claim 7 comprising, from said control unit, automatically switching operation of said breathing circuit from said EMG-controlled mode to said non-EMG controlled mode, with no manual intervention.

13. A ventilator comprising:

a breathing circuit adapted to interact with a patient, said breathing circuit being operable in a plurality of different modes to provide breathing assistance to the patient as actual breathing support generated in the breathing circuit and delivered to the patient as an output of the breathing circuit, including an EMG-controlled mode and a non-EMG-controlled mode;

a control unit that operates said breathing circuit in a selected one of said plurality of modes;

a registration unit that registers said actual breathing support provided by the breathing circuit to the patient; and said control unit being connected to said registration unit and being supplied with an EMG signal from the patient, said control unit being configured to determine, from an output of said registration unit and said EMG signal, whether synchrony exists based on a time relationship between said EMG signal and said actual breathing support and, if said synchrony is determined to exist while said control unit is operating said breathing circuit in said non-EMG-controlled mode, said control unit being configured to cause a switch from operation of said breathing circuit in said non-EMG controlled mode to operation in said EMG-controlled mode.

14. A ventilator as claimed in claim 13 wherein said control unit is configured to operate said breathing circuit to a support ventilation mode, as said non-EMG-controlled mode.

15. A ventilator as claimed in claim 13 wherein said control unit is configured to determine whether said synchrony is present based on a relationship between inspiration time and total breath time for at least one breath determined from said EMG signal.

16. A ventilator as claimed in claim 13 wherein said control unit is configured to determine whether said synchrony is present based on a relationship between inspiration time and expiration time for at least one breath determined from said EMG signal.

17. A ventilator as claimed in claim 13 wherein said control unit is configured to automatically switch operation of said breathing circuit from said non-EMG-controlled mode to said EMG controlled mode, with no manual intervention.

18. A method for providing breathing assistance to a patient comprising the steps of:

operating a breathing circuit to interact with a patient in selected one of a plurality of different modes to provide breathing assistance to the patient as actual breathing support generated in the breathing circuit and delivered to the patient as an output of the breathing circuit, including an EMG-controlled mode and a non-EMG-controlled mode;

in a registration unit, automatically registering said actual breathing support provided by the breathing circuit to the patient; and supplying a control unit connected to said registration unit with an EMG signal from the patient and with an output from said registration unit and, in said control unit, automatically determining, from said output of said registration unit and said EMG signal, whether synchrony exists based on a time relationship between said EMG signal and said actual breathing support and, if said synchrony is determined to exist while said breathing circuit is operating in said non-EMG-controlled mode causing, from said control unit, a switch from operation of said breathing circuit in said non-EMG controlled mode to operation in said EMG-controlled mode.

19. A method as claimed in claim 18 comprising, from said control unit operating said breathing circuit in a support ventilation mode, as said non-EMG-controlled mode.

20. A method as claimed in claim 18 comprising, in said control unit, determining whether said synchrony is present based on a relationship between inspiration time and total breath time for at least one breath determined from said EMG signal.

21. A method as claimed in claim 18 comprising in said control unit, determining whether said synchrony is present based on a relationship between inspiration time and expiration time for at least one breath determined from said EMG signal.

22. A method as claimed in claim 18 comprising, from said control unit, automatically switching operation of said breathing circuit from said non-EMG-controlled mode to said EMG controlled mode, with no manual intervention.

23. A ventilator comprising:

a breathing circuit adapted to interact with a patient, said breathing circuit being operable in a plurality of different modes to provide breathing assistance to the patient as actual breathing support generated in the breathing circuit and delivered to the patient as an output of the breathing circuit, including an EMG-controlled mode and a non-EMG-controlled mode;

a control unit that operates said breathing circuit in a selected one of said plurality of modes;

a registration unit that registers said actual breathing support provided by the breathing circuit to the patient; and said control unit being connected to said registration and being supplied with an EMG signal from the patient, said control unit being configured to determine, from an output of said registration unit and said EMG signal, whether an asynchrony exists based on a comparison of respiratory rates between said EMG signal and said actual breathing support and, if said asynchrony is determined to exist while said control unit is operating said breathing circuit in said EMG-controlled mode, said control unit being configured to cause a switch from operation of said breathing circuit in said EMG controlled mode to operation in said non-EMG-controlled mode.

24. A ventilator as claimed in claim 23 wherein said control unit is configured to determine whether said asynchrony is present by comparing an actual respiratory rate represented by the output of said registration unit, and a calculated respiratory rate calculated from said EMG signal.

25. A method for providing breathing assistance to a patient, comprising the steps of:

operating a breathing circuit to interact with a patient in selected one of a plurality of different modes to provide breathing assistance to the patient as actual breathing support generated in the breathing circuit and delivered to the patient as an output of the breathing circuit, including an EMG-controlled mode and a non-EMG-controlled mode;

in a registration unit, automatically registering said actual breathing support provided by the breathing circuit to the patient; and supplying a control unit connected to said registration with an EMG signal from the patient and with an output from said registration unit and, in said control unit, automatically determining, from said output of said registration unit and said EMG signal, whether an asynchrony exists based on a comparison of respiratory rates between said EMG signal and said actual breathing support and, if said asynchrony is determined to exist while said control unit is operating said breathing circuit in said EMG-controlled mode causing, from said control unit, a switch from operation of said breathing circuit in said EMG controlled mode to operation in said non-EMG-controlled mode.

26. A method as claimed in claim 25 comprising, in said control unit, determining whether said asynchrony is present by comparing an actual respiratory rate represented by the output of said registration unit, and a calculated respiratory rate calculated from said EMG signal.

27. A ventilator comprising:

a breathing circuit adapted to interact with a patient, said breathing circuit being operable in a plurality of different modes to provide breathing assistance to the patient as actual breathing support generated in the breathing circuit and delivered to the patient as an output of the breathing circuit, including an EMG-controlled mode and a non-EMG-controlled mode;

a control unit that operates said breathing circuit in a selected one of said plurality of modes;

a registration unit that registers said actual breathing support provided by the breathing circuit to the patient; and said control unit being connected to said registration and being supplied with an EMG signal from the patient, said control unit being configured to determine, from an output of said registration unit and said EMG signal, whether synchrony exists based on a comparison of respiratory rates between said EMG signal and said actual breathing support and, if said synchrony is determined to exist while said control unit is operating said breathing circuit in said non-EMG-controlled mode, said control unit being configured to cause a switch from operation of said breathing circuit in said non-EMG controlled mode to operation in said EMG-controlled mode.

28. A ventilator as claimed in claim 27 wherein said control unit is configured to determine whether said synchrony is present by comparing an actual respiratory rate represented by the output of said registration unit, and a calculated respiratory rate calculated from said EMG signal.

29. A method for providing breathing assistance to a patient, comprising the steps of:

operating a breathing circuit to interact with a patient in selected one of a plurality of different modes to provide breathing assistance to the patient as actual breathing support generated in the breathing circuit and delivered to the patient as an output of the breathing circuit, including an EMG-controlled mode and a non-EMG-controlled mode;

in a registration unit, automatically registering said actual breathing support provided by the breathing circuit to the patient; and supplying a control unit connected to said registration with an EMG signal from the patient and with an output from said registration unit and, in said control unit, automatically determining, from said output of said registration unit and said EMG signal, whether synchrony exists based on a comparison of respiratory rates between said EMG signal and said actual breathing support and, if said synchrony is determined to exist while said control unit is operating said breathing circuit in said non-EMG-controlled mode causing, from said control unit, a switch from operation of said breathing circuit in said non-EMG controlled mode to operation in said EMG-controlled mode.

30. A method as claimed in claim 29 comprising, in said control unit, determining whether said synchrony is present by comparing an actual respiratory rate represented by the output of said registration unit, and a calculated respiratory rate calculated from said EMG signal.

* * * * *